United States Patent
Klotz Rabello et al.

(10) Patent No.: US 11,642,657 B2
(45) Date of Patent: May 9, 2023

(54) METHOD FOR PREPARING A CATALYST FOR ONE-STEP PRODUCTION OF BUTADIENE FROM ETHANOL, CATALYST AND USE THEREOF

(71) Applicants: Petróleo Brasileiro S.A.—Petrobras, Rio de Janeiro (BR); Instituto Nacional De Tecnología—INT, Rio de Janeiro (BR)

(72) Inventors: Carlos Rene Klotz Rabello, Rio de Janeiro (BR); Alexandre Gaspar De Barros, Rio de Janeiro (BR); Luciano Honorato Chagas, Santos Dumont (BR); Lucia Gorenstin Appel, Rio de Janeiro (BR); Priscila Da Costa Zonetti, Rio de Janeiro (BR); Michelly Távora Rodrigues, Belford Roxo (BR)

(73) Assignees: Petróleo Brasileiro S.A.—Petrobras, Rio de Janeiro (BR); Instituto Nacional De Tecnologia—INT, Rio de Janeiro (BR)

( * ) Notice: Subject to any disclaimer, the term of this patent is extended or adjusted under 35 U.S.C. 154(b) by 0 days.

(21) Appl. No.: 17/942,824

(22) Filed: Sep. 12, 2022

(65) Prior Publication Data
US 2023/0084913 A1 Mar. 16, 2023

(30) Foreign Application Priority Data
Sep. 13, 2021 (BR) .................. 10 2021 018172 9

(51) Int. Cl.
*B01J 23/08* (2006.01)
*B01J 23/06* (2006.01)
(Continued)

(52) U.S. Cl.
CPC ............. *B01J 23/08* (2013.01); *B01J 21/066* (2013.01); *B01J 21/08* (2013.01); *B01J 23/06* (2013.01);
(Continued)

(58) Field of Classification Search
CPC . B01J 23/08; B01J 21/066; B01J 21/08; B01J 23/06; B01J 37/0205; B01J 37/0236;
(Continued)

(56) References Cited

U.S. PATENT DOCUMENTS

2017/0226028 A1* 8/2017 Smith .................. C07C 67/03
2017/0260112 A1* 9/2017 Nishino ................ C07C 27/06
(Continued)

FOREIGN PATENT DOCUMENTS

CN 110575828 A 12/2019
JP 2014210755 A 11/2014
(Continued)

OTHER PUBLICATIONS

Baerdemaeker et al. (Apr. 2015) "Bimetallic Zn and Hf on Silica Catalysts for the Conversion of Ethanol to 1,3-Butadiene", ACS Catalysis, 5(6):3393-3397.
(Continued)

*Primary Examiner* — Ali Z Fadhel
(74) *Attorney, Agent, or Firm* — Mintz Levin Cohn Ferris Glovsky and Popeo, P.C.

(57) ABSTRACT

The present invention relates to a process for the production of butadiene by condensation of ethanol using a catalyst containing sillica-supported elements from group 3A and group 4B of the periodic table. The catalyst of the present invention has high activity and selectivity to butadiene in the synthesis reaction of said olefin from ethanol.

8 Claims, 1 Drawing Sheet

(51) Int. Cl.
  *B01J 21/06*     (2006.01)
  *B01J 21/08*     (2006.01)
  *B01J 37/02*     (2006.01)
  *B01J 37/08*     (2006.01)
  *C07C 1/22*      (2006.01)

(52) U.S. Cl.
  CPC ......... *B01J 37/024* (2013.01); *B01J 37/0205* (2013.01); *B01J 37/0236* (2013.01); *B01J 37/088* (2013.01); *C07C 1/22* (2013.01); *C07C 2521/06* (2013.01); *C07C 2521/08* (2013.01); *C07C 2523/06* (2013.01); *C07C 2523/08* (2013.01)

(58) Field of Classification Search
  CPC ......... B01J 37/024; B01J 37/088; C07C 1/22; C07C 2521/06; C07C 2521/08; C07C 2523/06; C07C 2523/08
  See application file for complete search history.

(56) References Cited

U.S. PATENT DOCUMENTS

2018/0208522 A1\* 7/2018 Cadran ................ C07C 1/20
2021/0275991 A1\* 9/2021 Kurita ................. B01J 37/082
2022/0234031 A1\* 7/2022 Li ...................... B01J 23/894
2022/0259120 A1\* 8/2022 Yagihashi ............... C07C 7/06

FOREIGN PATENT DOCUMENTS

JP   2015034151 A   2/2015
JP   2016023141 A   2/2016

OTHER PUBLICATIONS

Camacho et al. (Jun. 2020) "Techno-economic and Life-Cycle Assessment of One-Step Production of 1,3-Butadiene from Bioethanol Using Reaction Data under Industrial Operating Conditions", ACS Sustainable Chemistry & Engineering, 8:10201-10211(42 pages).

Chagas et al. (Nov. 2019) "The Role of the Oxygen Vacancies in the Synthesis of 1,3-Butadiene from Ethanol", ChemCatChem, 11 (22):5625-5632(26 pages).

Ochoa et al. (Jan. 2017) "Understanding the Role of Gallium as a Promoter of Magnesium Silicate Catalyts for the Conversion of Ethanol into Butadiene", ChemCatChem, 9(12):10 pages.

Pomalaza et al. (2020) "Ethanol-to-butadiene: the Reaction and Its Catalysts", Catalysis Science & Technology, 10(15):4860-4911.

\* cited by examiner

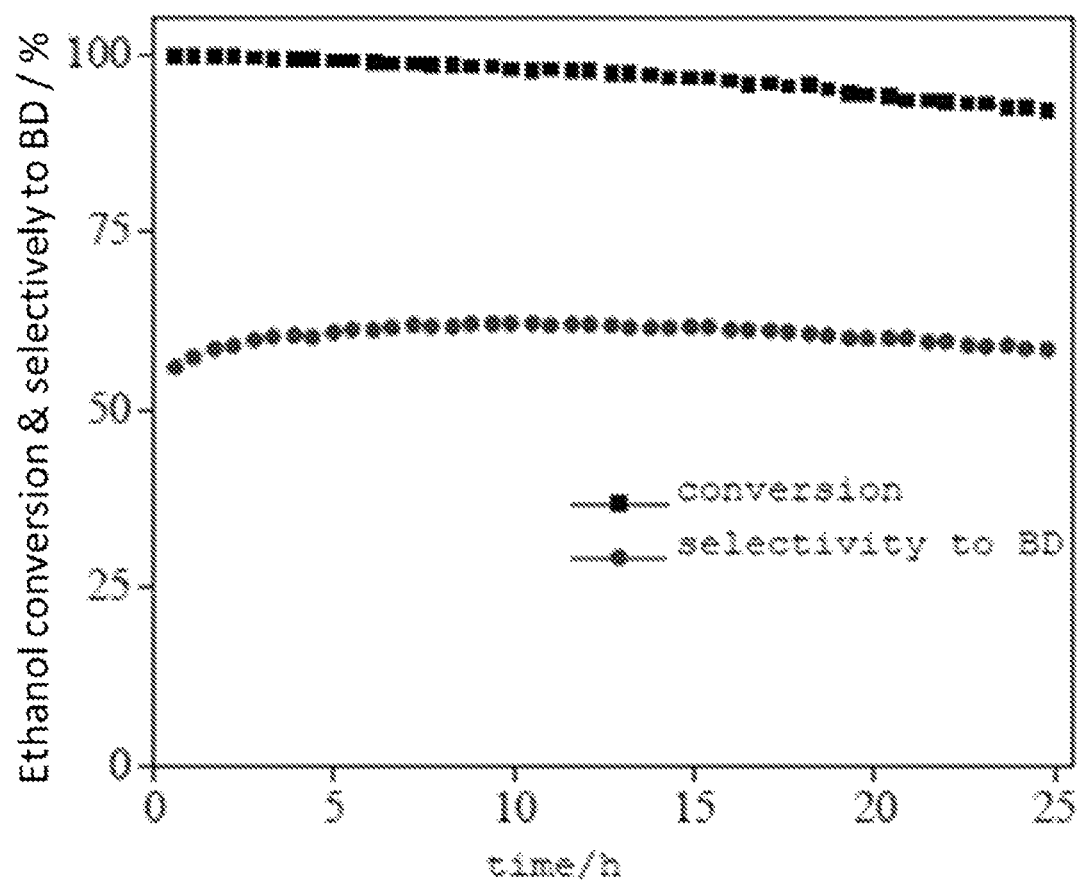

METHOD FOR PREPARING A CATALYST FOR ONE-STEP PRODUCTION OF BUTADIENE FROM ETHANOL, CATALYST AND USE THEREOF

CROSS-REFERENCE TO RELATED APPLICATION

This application claims priority to Brazilian Application No. 10 2021 018172 9, filed on Sep. 13, 2021, and entitled "METHOD FOR PREPARING A CATALYST FOR ONE-STEP PRODUCTION OF BUTADIENE FROM ETHANOL, CATALYST AND USE THEREOF," the disclosure of which is incorporated herein by reference in its entirety.

FIELD OF THE INVENTION

The present invention relates to the formulation of a catalyst, used in the production process of 1,3 butadiene from ethanol, which contains elements from group 3A and group 4B of the periodic table and silica, the object of which is to obtain high yields and selectivities in the production process of said olefin.

DESCRIPTION OF THE PRIOR ART 1,3-Butadiene is a commodity usually produced as a co-product of ethylene production via steam cracking of naphtha. This olefin is used as a raw material for the production of a variety of elastomers, polymeric resins and, mainly, synthetic rubbers, which are widely used in the automotive industry. Considering that the focus of the chemical industry is on issues associated with sustainability, the use of renewable raw materials in chemical processes is currently of great importance. Therefore, the production of butadiene from ethanol of renewable origin is a very interesting alternative for the viability of a whole chain of products or intermediates of renewable origin in the chemical industry.

Obtaining 1,3-butadiene from ethanol was recently reviewed by POMALAZA, G. et al. "Ethanol-to-butadiene: the Reaction and Its Catalysts", Catal. Sci. Technol., v. 10, p. 4860-4911. These researchers carried out an extensive and detailed work on the state of the art regarding information on catalytic systems, on reaction conditions and also on the kinetics and reaction mechanisms for the production of 1,3-butadiene from ethanol. There are two main processes disclosed in this document (the production of 1,3-butadiene from ethanol in one step (known as the Lebedev process) and the two-step production (known as Ostromislensky process). On the latter, there is a first reactor where ethanol is dehydrogenated to acetaldehyde and a second reactor where the conversion of ethanol/acetaldehyde to 1,3-butadiene takes place. Therefore, this literature review lists the main issues to be overcome for the economically viable production of 1,3-butadiene from ethanol, namely: high rate of catalyst deactivation, use of toxic compounds in catalyst formulations, and also relatively low selectivities and conversions that make the use of this reaction unfeasible as a commercial route for the production of 1,3-butadiene.

Hence, the production of 1,3-butadiene from ethanol in one step presents a great challenge regarding the definition of the composition of new catalysts, considering the following requirements: 1) catalysts must be active and selective in order to minimize the generation of ethene; 2) the new reaction systems should not consider the simultaneous addition of acetaldehyde together with ethanol in the reactor inlet stream, a strategy widely used in the state of the art, because, in this case, the process involves two steps, in view of generating said aldehyde from ethanol; 3) the use of toxic compounds must be avoided in the composition of catalytic systems; 4) finally, the use of zeolites in the composition of catalysts should be avoided due to their strong propensity to deactivate.

The general mechanism of butadiene synthesis from ethanol, accepted by the vast majority of researchers in the field, can be described from the following steps: initially, the dehydrogenation of ethanol occurs, forming acetaldehyde; then, this aldehyde condenses generating acetaldol, which is dehydrated to form crotonaldehyde; then, this compound is hydrogenated to crotyl alcohol via the MPV mechanism (Meerwein—Pondor f-Verley reaction); finally, this C4 alcohol dehydrates generating butadiene. In previous works, such as in CHAGAS, L. H. et al., (2019) "The Role of Oxygen Vacancies in the Synthesis of 1,3-butadiene from Ethanol", ChemCatChem, v. 11, p. 5525-5532, it was noted that the slow reaction step is the synthesis of acetaldehyde. In addition, the MPV mechanism in the synthesis in question is of great importance. If the catalyst is not very active in this hydrogenation, the generation of heavy compounds is favored, which leads to a reduction in the selectivity to butadiene and the deactivation of the catalysts according to the results obtained in studies made by CHAGAS, L. H. et al, 2019), The Role of Oxygen Vacancies in the Synthesis of 1,3-butadiene from Ethanol", ChemCatChem, v. 11, p. 5525-5532. The authors, who are the same in this document, showed that the addition of low levels of Zn to $ZrO_2$ (tetragonal), make this oxide behave as a catalyst in the generation of butadiene from ethanol. This system has high activity and reasonable selectivity values for butadiene. The increase in $ZrO_2$ activity with the addition of Zn is associated with an increase in the rate of acetaldehyde generation. The $Zn^{2+}$ ion enters the $ZrO_2$ tetragonal crystal lattice replacing the ZH+ and generating oxygen vacancies. This happens because $Zn^{2+}$ has a lower degree of oxidation than $Zr^{4+}$. These vacancies behave as strong basic Brönsted sites, abstracting the H from the ethoxides, derived from ethanol, forming acetaldehyde and thus promoting the slow step of butadiene synthesis. On the other hand, the behavior of these systems in the MPV step is only reasonable, which results in the formation not only of butadiene, but also of higher molecular weight compounds. Results obtained concerning the hydrogenation of acetone by ethanol via the MPV mechanism show that when Zr is added to $SiO_2$ the behavior of the new system is much superior to that of pure $ZrO_2$, as will be shown below.

References for obtaining butadiene from ethanol are found in patent literature and scientific papers, showing Cu, Zn, Mg, Zr, Ag, Hf and Ta as the most frequent elements. It should be noted that Ta and Hf are very unusual in the context of heterogeneous catalysis. Catalyst supports, in turn, refer to zeolitic and silica structures, the latter being much more used. It is worth mentioning that Cu, Zn, Ag are associated with the generation of acetaldehyde while the other elements refer to the aldol condensation reaction, MPV and dehydration.

Prior-art document JP2014210755 describes the preparation, by wet impregnation, of catalysts of the $M/X/SiO_2$ type, wherein M can be Na, Ba, La, and X can be Zr, Ta or Hf. If there are two components on the support, the preparation takes place by successive wet impregnations. The highest yield of butadiene is 30.3%, with selectivity of 50.9% and conversion of 59.5% to the $Zr/SiO_2$ catalyst. On the other hand, higher selectivity to butadiene (66.7%) is noted for catalyst Ba/Ta/SiO$_2$. However, conversion is only of 29.8%. Tests were carried out in a fixed bed, continuous-flow reactor, at 400° C., atmospheric pressure and ethanol/acetaldehyde/water/N2 ratio of 4:2:0.4:3.6 L·h$^{-1}$. It should be noted that, in addition to the low catalyst activity of the catalyst, the use of Ta leads to the use of precursors that have low solubility, which makes preparation procedures in the laboratory and possibly in the industry very difficult.

DE BAERDEMAEKER, T. et al. (2015), in "Bimetallic Zn and Hf on silica catalysts for the conversion of ethanol to 1,3-butadiene", ACS Catalysis, v. 5, p. 3393-3397, investigated bimetallic silica-supported catalysts for the conversion of ethanol to 1,3-butadiene. The combination of Hf (IV) and Zn (II), wherein hemimorphite (Zn silicate, mineral) was used as a source of Zn (II), resulting in a stable, active and selective catalyst with an ethanol conversion of 99.2% and a selectivity to butadiene of 71%, after 0.5 h to 10 h of reaction at 360° C., preceded by a reaction period of 3 h at 300° C. using a space velocity of 0.64 $g_{EtOH}g_{cat}^{-1}h^{-1}$. The best catalyst is a very atypical system, which uses a Zn mineral, and this can make reproduction of this catalyst difficult. In addition, the reaction conditions are very unusual.

Japanese patent JP2015034151 discloses obtaining butadiene from ethanol using a Mg silicate as a catalyst. The catalyst is synthesized via hydrothermal synthesis, using urea as a precipitating agent and may employ Co, N$_i$, Cu, Ga, In, Zn or Ag as additives. Obtaining butadiene is carried out at 350° C., atmospheric pressure, in a fixed bed reactor, under a continuous flow of ethanol (6.5% mol) diluted in N$_2$ for 6 hours. Contact time (W/F) is 0.03 $g_{cat}$·min·mL$_{EtOH}^{-1}$. The most expressive result is 94% ethanol conversion and 80% selectivity to butadiene using a catalyst containing 5% by mass of ZnO and Mg/Si ratio equal to 1. The results are interesting, but the low value of the ethanol concentration makes it difficult to reach a more secure assessment.

Ochoa, J. V. et al. (2017) "Understanding the Role of Gallium as a Promoter of Magnesium Silicate Catalyts for the Conversion of Ethanol into Butadiene", investigate the use of gallium in the formulation of catalysts for the conversion of ethanol to 1,3-butadiene, supported by MgO/SiO$_2$. The 1,3-butadiene molar base selectivities were in the range of 18.6 to 52.4%, and with ethylene formation in selectivities of 8.0 to 47.7%. It should be noted that this work presents relatively low selectivities to butadiene.

Japanese patent JP2016023141 discloses catalysts supported on ZrO$_2$/SiO$_2$ and other supports. The catalyst consists of Cu, Zn and Zr on silica and the reaction is preferably carried out between 300° C. and 600° C. These systems are used in the conversion of acetaldehyde and ethanol to 1,3-butadiene. As already pointed out, the Ostromislensky process involves two steps, with two reactors, which makes investment and operating costs high.

Patent CN110575828-A discloses ZrO$_2$/SiO$_2$ supported catalysts used in the Ostromislensky process. However, as already mentioned, this process requires two reactors, being less advantageous compared to the one-step process.

CAMACHO, C. E. C. et al. (2020) "Techno-economic and Life-Cycle Assessment of One-Step Production of 1,3-Butadiene from Bioethanol Using Reaction Data under Industrial Operating Conditions", ACS Sustainable Chem. Eng., v. 8, p. 10201-10211, report a process for producing 1,3-butadiene from ethanol in a one-step reaction with an Hf—Zn catalyst, wherein tests were performed at 360° C., under continuous flow of ethanol in N$_2$ and space velocity of (WHSV) of 0.64 h$^{-1}$, resulting in 87.1% ethanol conversion and 69.5% butadiene selectivity. The space velocity value is low which shows that the activity of these catalysts is low.

Thus, to solve the issues mentioned above, the present invention was developed through the formulation of an active and selective catalyst for the synthesis of butadiene from ethanol, composed of silica containing elements from group 3A and group 4B of the periodic table.

The catalyst of the present invention has high activity and selectivity in the synthesis reaction of butadiene from ethanol.

The present invention relates to the development of catalysts directed to the technological route of butadiene production, the investment in which is much lower than the conventional production process (steam cracking of naphtha). This process has high Capital Expenditure and is extremely energy intensive, having a high consumption of utilities. In addition to this particular aspect, this new technological route enables the production of butadiene from renewable raw material.

BRIEF DESCRIPTION OF THE INVENTION

The present invention relates to a process for the production of butadiene by condensation of ethanol using a catalyst containing sillica-supported elements from group 3A (Ga) and group 4B (Hf) of the periodic table. More particularly, the present invention relates to an active and selective catalyst for the synthesis of butadiene from anhydrous or hydrated ethanol. The catalyst of the present invention has high activity and selectivity to butadiene in the synthesis reaction of said olefin from ethanol.

BRIEF DESCRIPTION OF THE DRAWINGS

The present invention is described in detail below, with reference to the enclosed drawing, which represents an embodiment of the same in a schematic manner, not limiting the inventive scope. The drawing describes:

FIG. 1 illustrates a graph of the behavior of Ga/Hf/SiO$_2$ catalyst in time-on-stream, according to the present invention.

DETAILED DESCRIPTION OF THE INVENTION

The method of preparing the catalyst for use in the production of butadiene, according to the present invention, comprises the following steps:

a) Adding to SiO$_2$, through dry impregnation, an element from group 4B of the periodic table, preferably Hf, using an aqueous solution of the chloride of this metal;

W drying the solid obtained in a) at 120° C. for 10 hours and calcining at 500° C. for 4 hours at a rate of 10° C.·min$^{-1}$ under synthetic air flow (60 mL·min$^{-1}$);

c) impregnating the solid obtained in b) with an aqueous solution of a metal ion nitrate of the element from group 3A of the periodic table, preferably element Ga;

d) drying the catalyst obtained in c) at 120° C. for 10 hours and calcining at 500° C. for 4 hours at a rate of 10° C.·min$^{-1}$, under synthetic air flow (60 mL·min$^{-1}$).

The catalyst thus prepared has in its composition 0.1% to 5% by weight of gallium with respect to the support and 0.5% to 15% by weight of hafnium with respect to the support.

The butadiene synthesis reaction via ethanol condensation using catalysts containing silica-supported elements from group 3A (Ga) and group 4B (Hf) of the periodic table was carried out in a Plug Flow Reactor (PFR) at a pressure from 1 to 5 atm, temperatures from 250 to 450° C. and space velocity (WHSV) between 1 to 15 $g_{ethanol} \, g_{cat} h^{-1}$.

EXAMPLES

The examples below illustrate a few embodiments of the invention, and prove its feasibility, not constituting any form of limitation of the invention.

Example 1: Preparation of Catalysts Doped with Elements from Group 3A and Group 4B of the Periodic Table The preparation of the catalysts took place via successive dry impregnation using $SiO_2$. Initially, the support was impregnated with an aqueous solution of the element from group 4B, followed by drying at 120° C. for 10 hours and calcination at 500° C. for 4 hours (10° C.·$min^{-1}$) under synthetic air flow (60 mL·$min^{-1}$). Then, the materials were impregnated with an aqueous solution of a metal ion nitrate of elements from group 3A of the periodic table. These catalysts were also dried and calcined under the same conditions already described in the addition of the element from group 4B.

Example 2: The Catalytic Tests were Carried Out in a PFR Micro Reactor

The data presented in Table 1 was obtained after approximately 3 hours of reaction. The analyzes of the gas mixture composition at the reactor outlet and inlet were carried out by gas chromatography.

The catalysts used were $X/MO_2/SiO_2$, wherein M=Zr or Hf=4% at. and X=Ga, In or Cd=0.6% at., wherein Si=95.4% at.

The tests in Table 1 were performed under experimental conditions of temperature, pressure, flow rate and ethanol: $N_2$ ratios of 385° C., 1 atm, 25 mL·$min^{-1}$, 3:97 or 20:80 v/v, respectively.

The results in Table 1 show that, comparing the Cd, In and Ga promoters (tests 1, 2 and 3), when $Hf/SiO_2$ is used, the latter presents greater activity and selectivity to butadiene.

Comparing tests 3 and 4 (low ethanol concentration) that differ in terms of the use of Zr and Hf, it is found that the presence of the latter results in greater selectivity to butadiene, while the conversion of both has very similar values.

Comparing the same catalysts employing a 6.5 times greater content of ethanol in the reaction mixture, tests 6 and 7, it is noted again that, for Hf, selectivity to butadiene is greater than for Zr, while the conversion is virtually equal. These results also show that, in the presence of Hf, the C balance approaches 100%.

Test 5 shows that without Ga the activity and selectivity to butadiene of the $Hf/SiO_2$ system is very low.

Test 8 shows that using 400 mg of $Ga/Hf/SiO_2$ and a concentration of 20% ethanol in $N_2$ it is possible to achieve high values of conversion and selectivity to butadiene.

TABLE 1

Behavior of catalysts in the synthesis of butadiene from ethanol. $C_{ethanol}$, m, X, $S_{BD}$, $S_{ethene}$, $S_{act}$, C, $Y_{BD}$ correspond to ethanol: N2 v/v ratio, catalyst mass, ethanol conversion, selectivities to 1,3-butadiene, ethylene, acetaldehyde, balance of carbon and yield in 1,3-butadiene, respectively.

| | catalyst | $C_{ethanol}$/% | m/g | X/% | $S_{BD}$/% | $S_{ethene}$/% | $S_{act}$/% | C/% | $Y_{BD}$/% |
|---|---|---|---|---|---|---|---|---|---|
| 1 | $Cd/Hf/SiO_2$ | 3 | 0.1 | 94.2 | 43.4 | 24.8 | 5.0 | 85.2 | 40.9 |
| 2 | $In/Hf \, SiO_2$ | 3 | 0.1 | 97.2 | 57.0 | 5.1 | 16.6 | 78.2 | 36.0 |
| 3 | $Ga/Hf/SiO_2$ | 3 | 0.1 | 99.5 | 62.4 | 11.2 | 6.5 | 92.2 | 62.1 |
| 4 | $Ga/Zr/SiO_2$ | 3 | 0.1 | 97.1 | 58.3 | 13.3 | 8.6 | 93.7 | 56.6 |
| 5 | $Hf/SiO_2$ | 20 | 0.4 | 53.8 | 11.3 | 33.8 | 2.1 | 52.4 | 6.1 |
| 6 | $Ga/Zr/SiO_2$ | 20 | 0.3 | 92.4 | 54.4 | 15.6 | 7.4 | 87.7 | 50.3 |
| 7 | $Ga/Hf/SiO_2$ | 20 | 0.3 | 91.5 | 67.7 | 9.8 | 6.6 | 94.2 | 61.9 |
| 8 | $Ga/Hf/SiO_2$ | 20 | 0.4 | 97.7 | 71.0 | 9.9 | 4.0 | 95.9 | 69.4 |

Example 3: Isoconversion Test Results

Table 2 shows the results obtained from Isoconversion tests for catalyst Ga/Zr/SiO$_2$ and Ga/Hf/SiO$_2$. The testes of Table 2 were performed under experimental conditions of temperature, pressure, flow rate, ethanol:N$_2$ ratio of 385° C., 1 atm, 25 mL·min$^{-1}$, 3:97 v/v, respectively.

Comparing tests 9 and 10, it can be seen that to achieve 55% conversion (isoconversion) in the case of the Hf-based catalyst, a space velocity (WHSV) 50% greater than that of the Zr-containing system is used. This results shows that the Hf catalyst is more active than that of Zr. It has been further observed that selectivity to butadiene is slightly lower than that of Zr.

TABLE 2

Isoconversion tests (50%), with WHSV being the space velocity used. The other symbols are the same as in Table 1.

| catalysts | WHSV/g$_{etanol}$g$_{cat}$h$^{-1}$ | S$_{BD}$/% | S$_{ethene}$/% | S$_{acet}$/% |
|---|---|---|---|---|
| 9 Ga/Zr/SiO$_2$ | 6.2 | 27.6 | 11.7 | 30.2 |
| 10 Ga/Hf/SiO$_2$ | 9.6 | 24.7 | 9.8 | 32.8 |

Example 4: Behavior of Catalyst Ga/Hf/SiO$_2$, According to the Present Invention FIG. 1 shows the result of the stability test of approximately 25 hours for catalyst Ga/Hf/SiO$_2$. The variables mass, temperature, pressure, flow rate, ethanol:N$_2$ ratio were 100 mg, 385° C., 1 atm, 25 mL·min$^{-1}$, 3:97 v/v, respectively.

As can be seen in FIG. 1, after 25 hours of reaction, the ethanol conversion decreases from 99.6% to 92.1%, while the selectivity to butadiene reaches a maximum of around 62%, ending the run at around 56%. Furthermore, FIG. 1 shows a reasonably stable behavior considering the catalyst mass used.

Finally, the results show that the catalysts containing Hf and Ga are very active, selective to butadiene and reasonably stable.

It should be noted that, although the present Invention has been described in relation to the examples above, it may undergo changes and adaptations by skilled artisans, depending on the specific situation, but provided that it is within the Inventive scope defined herein.

The invention claimed is:

1. A method for preparing a catalyst for one-step production of butadiene from ethanol comprising the following steps:
    (a) adding an element from group 4B of the periodic table to SiO$_2$ support, through impregnation with an aqueous solution of the chloride of this metal;
    (b) drying the solid obtained in a) at 120° C. for 10 h and calcining at 500° C. for 4 h under air flow;
    (c) impregnating the solid obtained in b) with an aqueous solution of a metal ion nitrate of an element from group 3A of the periodic table;
    (d) drying the solid obtained in c) at 120° C. for 10 h and calcining at 500° C. for 4 h under air flow.

2. The method according to claim 1, characterized in that the element from group 3A of the periodic table is gallium and the element from group 4B of the periodic table is hafnium.

3. A catalyst obtained according to the method defined in claim 1, characterized by comprising in its composition: a) the SiO$_2$ support; b) the elements from group 3A and group 4B of the periodic table.

4. The catalyst according to claim 3, characterized in that the element from group 3A is gallium.

5. The catalyst according to claim 4, characterized by having a gallium content between 0.1% and 5% by weight in relation to the support.

6. The catalyst according to claim 3, characterized in that the element from group 4B is hafnium.

7. The catalyst according to claim 6, characterized by having a hafnium content between 0.5% and 15% by weight in relation to the support.

8. A process of production of butadiene from ethanol comprising contacting ethanol with the catalyst of claim 3 in a continuous-flow tubular reactor at a temperature between 250 and 450° C., pressure between 1 and 5 atm and space velocity (WHSV) between 1 and 15 g$_{ethanol}$g$_{cat}$h$^{-1}$.

* * * * *